United States Patent [19]

Nakagawa et al.

[11] Patent Number: 4,587,020

[45] Date of Patent: May 6, 1986

[54] CHROMATOGRAPHIC PLATE

[75] Inventors: Yuzo Nakagawa, Osaka; Kouji Iwatani, Hyogo; Tetsuro Kadono, Osaka, all of Japan

[73] Assignee: Shionogi & Company, Ltd., Osaka, Japan

[21] Appl. No.: 641,552

[22] Filed: Aug. 16, 1984

[30] Foreign Application Priority Data

Aug. 17, 1983 [JP] Japan .................. 58-150605

[51] Int. Cl.⁴ .......................................... B01D 15/08
[52] U.S. Cl. ................... 210/658; 210/198.3; 422/70; 436/162
[58] Field of Search ............... 210/198.3, 658; 422/70; 436/162

[56] References Cited

U.S. PATENT DOCUMENTS

| 3,279,307 | 10/1966 | Wilks, Jr. | 210/198.3 |
| 3,318,451 | 5/1967 | Przybylowicz et al. | 210/198.3 |
| 3,600,306 | 8/1971 | Tocci | 210/198.3 |
| 3,878,100 | 4/1975 | Bixler | 210/198.3 |
| 4,273,653 | 6/1981 | Uihlein | 210/198.3 |

Primary Examiner—John Adee
Attorney, Agent, or Firm—Birch, Stewart, Kolasch & Birch

[57] ABSTRACT

A chromatographic plate comprising a support having a plurality of linear grooves engraved on the rear is disclosed. Each of said grooves have a uniform depth of a half or less as large as the thickness of the support and serves to guide a cutter. After the chromatographic development, the support may easily be cloven along the grooves into strips together with an adsorbent layer carried by the front of the support to give a sample holder for mass spectrometry.

12 Claims, 10 Drawing Figures

CHROMATOGRAPHIC PLATE

BACKGROUND OF THE INVENTION

1. Field of the Invention

The present invention relates to chromatographic plates. In paticular, it is concerned with those constructed so that, after a mixture sample is separated into its components by chromatographic development, the sample can easily be identified and quantitatively determined by mass spectrometry for each of the components.

2. Description of the Prior Art

For a mass spectrometry of a mixture sample containing minute components, so-called GC/MS system, which combines a preceding separating step by gas chromatography with mass spectrometry analysis has recently been developed and is now in frequent use. This system, however requires an extraordinarily expensive GC/MS system as a matter of course. Furthermore, this system has a problem in that it is hardly applicable to analyses of scarcely vaporizable compounds and of an unstable compound that decomposes or degrades by heat during the process of gas chromatography. In those cases, the sample should necessarily be modified by alkylsilylation or acylation in order to make its vaporization easy, but it is a serious drawback to impose an additional task to operators. Moreover, some of the alkylsilylated or acylated compound obtained by the additional process might inevitably be altered in part thereof.

A mixture sample containing a thermally-unstable compound, which may be changed during the gas-liquid chromatography into a degraded compound which cannot be properly determined, may be developed on a laboratory-prepared thin layer chromatographic plate to be separated into respective components. Part of the adsorbent of thin layer at the specified spot is scraped off to be extracted with a solvent and the extracted component can then be introduced into the mass spectrometer from its direct introduction unit.

However, such manipulations of scraping and solvent extraction are not only a nuisance to the operator but also are hardly performed with sufficient accuracy and will bring about a loss in the sample, i.e., an incorrect quantitative determination value. Furthermore, some of the compounds might be subjected to alteration such as oxidation during the operation.

Incidentally, a rod-type chromatgraphic element disclosed in U.S. Pat. No. 3,839,205 owned by the applicant is made available for performing FID (Flame Ionization Detection) as its principal purpose, but it is found that the element may also be used as a sample holder for mass spectrometry.

However, this rod-type chromatographic element is not necessarily sufficient in the following points. Namely, in order to perform FID, a high degree of heat resistant property is required of each of the supporting rods, adsorbent and binding agent. The supporting rod, for instance, must be quartz and the binding agent must be borosilicate glass, crystallized glass or the like. This condition may not necessarily be required of the sample holder for mass spectrometry and will make the element unduly expensive. Furthermore, since the properties of the adsorbent thin layer may vary with individual elements, specified components to be detected might show different Rf values in the individual elements of the same lot which are prepared at the same time; thus the comparison with an authentic sample might often be made difficult even if the authentic sample is developed simultaneous with and in parallel with the sample to be determined.

In an attempt to overcome the abovementioned deficiency, the present inventors have invented a sample holder which is capable of separating a mixture sample into respective components prior to or during the mass spectrometry (See, for instance, U.S. Pat. No. 4,267,457). The abovementioned invention uses, as the separating means, the principle of thin-layer chromatography or gas-liquid chromatography enable the mass spectrometer to give molecular ions of the respective components, successively.

This is useful for mass spectrometry of a mixture sample containing a plurality of minute components though it is still unsatisfactory in its convenience for introducing the cut support headed by the developed spot into an ionization chamber of a mass spectrometer in the case wherein the sample is a mixture composed of two or, in particular, three or more components having insufficient differences in Rf values in the chromatogram.

On the other hand, the specification of U.S. Pat. No. 3,896,661 discloses a method and an apparatus for embodying the method for obtaining a mass spectrum successively by introducing a thin-layer chromatographic plate which has a developed chromatogram thereon into an ionization chamber as it is and stepwisely transferring the plate so that each of the positions of the component spots might coincide with that of the ion source successively.

According to this system, the handling of the chromatogrphic plate is convenient, though it is difficult to put the system to practical use. Even if this system is embodied, it would become very expensive, in that it requires an extremely large ionization chamber, and a complex and elaborate apparatus for the stepwise transfer of the plate.

SUMMARY OF THE INVENTION

The present invention is proposed to eliminate the drawbacks of the abovementioned prior art and of overcoming the problem inherent to the prior art; and, according to the present invention, there is provided a chromatographic plate which comprises a support having a plurality of linear grooves engraved on the rear. In the abovementioned plate, each of the grooves has a uniform depth of a half or less as large as the thickness of the support and serves to guide a cutter which may be a simple "ampule cutter". In some instances, the linear grooves may be grouped into first and second rows crossing each other at right angles and the grooves in the first row may have larger spacings between the adjoining two than those held by the grooves in the second row.

DETAILED DESCRIPTION

Figure 1:
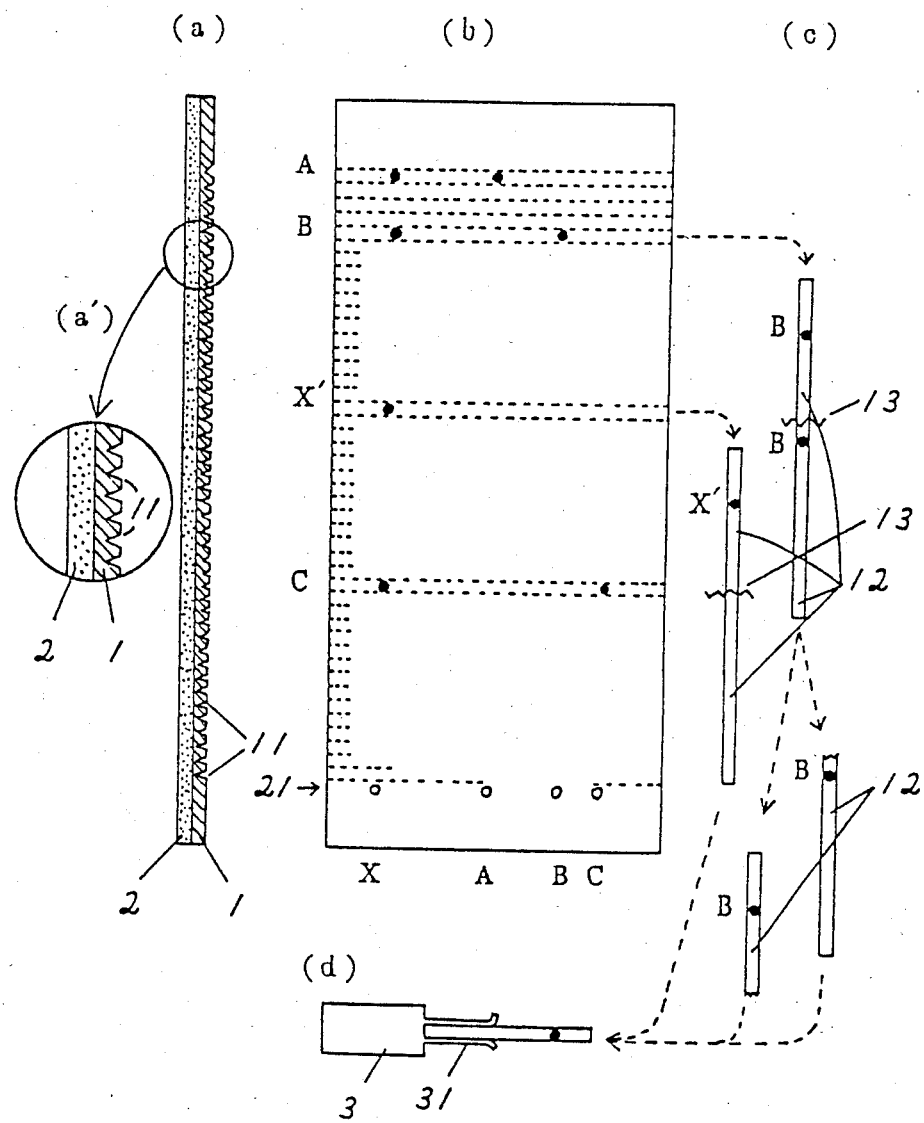
FIGS. 1 and 2, each schematically represent a chromatographic plate, an embodiment of the present invention, wherein (a) is its cross sectional view, (a') is a partly enlarged view thereof, (b) is a plan view in a state wherein a mixture sample and authentic samples are developed, (c) is a plan view of the strip cloven from the plate and (d) is a schematic view showing a state wherein the cloven strip is set on a holder fastening tool of the apparatus as a sample holder for mass spectrometer.

In the abovementioned plate, an adsorbent layer carried by the front of the support may comprise a chromatographically-active adsorbent and a suitable binding agent therefor.

The chromatographically-active adsorbent may be any adsorbent having chromatographic activity but preferably be adsorbents for thin-layer chromatography. These can be exemplified as silica gel, alumina, diatomaceous earth, zeolite, aluminum silicate and porous glass powder (one represented by trade name "Porous Vycor" available from Corning Glass Works Co.,Ltd.,U.S.A.; prepared by treating high silicate glass with an acid to dissolve all of the acid-soluble component out and to form numerous micro pores by the dissolution). If the adsorbent has a dehydrogenating catalytic action, it is better to avoid the use of such an adsorbent in separating a sample which contains a compound having a possibility of being involved in a dehydrogenation reaction.

As the support, glass is usually used though any other heat-resistant and chemically-inert material can be used as far as it can be modified to be cloven easily into strips together with the adsorbent layer by engraving the linear grooves on the rear.

As the binding agent used for bonding the adsorbent particles with each other as well as for gluing the adsorbent layer to the support, any material can be selected from a variety of the material as long as it does not affect the chromatographic development and/or mass spectrometry of the sample. The glass particle binder disclosed in Pat. No. 907,248=U.S. Pat. No. 3,839,205 granted to the applicant is a preferred one but has a drawback in that it requires an additional task of baking during the preparing process. As the binding agent which does not require the baking, there is exemplified any organic binder which fulfils the above requirements, e.g., sodium polyacrylate, polyacrylamide, polyvinylformal, polyisocyanate, homopolymer or copolymers of esters of acrylic acids or methacrylic acids and glycols, mixtures of one or more of them with colloidal silica and the like.

If the unknown sample has no absorption band in the visible ray region and is therefore colorless, then it is desirable to include a fluorescent material in the adsorbent layer for the convenience of handling. As the fluorescent material, any crystalline material of the activator-type can be used and its inclusion in an amount of from 1/30 to 1/10 of that of the adsorbent is sufficient for the purpose. Spots of the sample to be detected may appear as shadows cast on the surrounding luminescent surface by absorbing ultraviolet ray irradiated to the fluorescent material.

The linear grooves are usually arranged in a direction perpendicular to the chromatogram development direction, though a plate which has a row of the grooves parallel to the development direction may be used when developing a sample of two or more components, whose respective Rf values will give the spots of sufficient distance therebetween. The spacing between the adjoining two grooves is suitably constant (normally, about 2 mm). Each of the linear grooves desirably has a uniform depth of a half or less as large as the thickness of the support and a V-shaped section but may be of any shape as far as it can accomodate and guide a tip of the glass cutter.

If a tip of the glass cutter applied to the bottom of the groove is glided gently along the groove, the support can easily be cloven into strips by an extremely small flexing force together with the adsorbent layer carried by the front.

When the plate is made of glass, the grooves may be provided by dies at the molding of the plate. If ready-made sheet glass is available, the grooves may be formed by a cutter (grinding wheel) or the like before or after the formation of the adsorbent layer.

Meanwhile, in addition to the row of the grooves with dense spacings, another row of grooves with sparse spacings which crosses the former row at right angle may be provided. By doing abovementioned, it can be made possible to obtain a cloven strip which carrys a stain of the target substance near the tip thereof and has a supporting segment(stem) of sufficient length, depending partly on the manner of titrating the sample. Therefore, it is easy to set the strip on a clamping means of a sample holding unit of a mass spectrometer and to simplify its introduction into the ionization chamber because the size of the strip is relatively compact. By arranging the plate as previously described, the chromatographic plate of the present invention can be utilized as an excellent sample holder for a mass spectrometer or a rod FID. When utilizing it as the sample holder for a mass spectrometer, a mixture sample, containing a minute component which may be changed to another substance by thermal decomposition during the process in GC/MS system and therefore may not give a molecular ion, can successfully be separated into the respective components by the chromatographic development and then determined by mass spectrometry to give a molecular ion. Furthermore, the plate can be constructed with relatively inexpensive materials if the heat resistant property of the materials is kept within a limit that is required for the mass spectrometry only.

In addition to this, since the chromatographic plate of the present invention permits parallel and simultaneous development of both the sample to be determined and the authentic sample on a single adsorbent layer, it is easy to make the identification of the position of the separated spot of the target component in the sample to be determined by making reference to that of the authentic sample. By doing so, a sample holder which carrys the spot near the tip thereof can be obtained.

Even in the cases wherein the distance between the spots of the respective components thus separated is insufficient, the loss of the sample is small as compared with the case of the troublesome scraping manipulation because a sample holder is obtained for each of the respective components. Namely, accurate analytical data can be obtained by rapid operation.

Incidentally, in the case of the chromatographic plate of the present invention which has the linear grooves arranged in parallel with each other and in the direction of chromatogram development, the strip can also be used for performing FID. In that case, the materials are required to have a high degree of heat resistant property as previously described. It however is convenient because the positions of the developed spots are first confirmed by FID and then mass spectrometry is performed on a sample holder of a strip which had been in parallel with or adjacent to the strip which had previously been used in the FID detection and cloven from the same plate.

In a case wherein a much higher degree of separation of the respective components in the mixture sample is required, a preparatory concentrating zone whose chromatographic activity is intentionally reduced to some extent may preferably be provided on the adsorbent layer in addition to a zone being in an exclusive use for chromatographic development. The sample titrated on this preparatory concentrating zone will be concentrated by an ascending developing solvent near the boundary shared commonly by the developing and concentrating zones, and then shifted to the developing zone to give linear or rectangular spots extended in the direction perpendicular to the development direction.

This is particularly advantageous in obtaining a definite separation of the components whose Rf values are so close that the peripheral parts of the developed spots might be overlapped with each other unless no other measure is taken.

In the case of the plate whose binding agent is glass fine particles and the adsorbent layer is formed by sintering, the above mentioned concentrating zone may be a sintered thin layer solely composed of glass particles and no adsorbent.

DESCRIPTION OF THE PREFERRED EMBODIMENT

In the following description, the present invention will be elucidated in more detail by referring to the drawing schematically showing embodiments thereof.

EXAMPLE 1

(Plate with the linear grooves of the direction which crosses the development direction at a right angle)

FIG. 1 schematically illustrates the plate. Wherein, (a) is its sectional view, (a') is a partly enlarged view thereof, (b) is a plan view of the plate on which a mixture sample is developed, (c) is a strip after being cloven and (d) indicates the same strip in a state of being secured by a clamp means of a mass spectrometer as a sample holder therefor.

Details of this plate will be indicated together with the Measurement (1) which follows.

Namely, the chromatographic plate shown in FIGS. 1 (a),(a') and (b) composed of glass plate 1 and adsorbent layer 2 on its front has a row of linear grooves 11 arranged in parallel with each other on the rear of the plate in a direction which crosses the chromatgram development direction at a right angle. A mixture sample X containing unknown substance X' and authentic samples A,B and C are titrated at the sites 21 (indicated by blank circles) and subjected to ascending development by a known method; then the substances in the sample ascend in accordance with the intrinsic Rf values of the respective substances to give the illustrated chromatogram after a given time period. As seen in the chromatogram, the respective substances are separated at sites (indcated by solid black circles) which correspond to A,B,X' and C, respectively.

If the substance in the sample is colorless, the site of the spot can nevertheless be detected by virtue of the fluorescent material contained in the adsorbent and the intrinsic ultra-violet ray absorption of the substance. After the site of the spot is found, the plate is cloven into strips as shown in (c), first by sliding a glass cutter whose tip is applied to the bottom of the linear groove along the groove and then by applying a flexing force of the finger tips. These strips are then shortened in a required length at given points indicated by wave lines 13 and the stems thereof 12 are secured by the clamps 3, 31 (resilient tips) of the sample holding unit of a mass spectrometer as indicated by (d) to be introduced into the ionization chamber.

As is found there, since the unknown mixture sample X can be developed simultaneously and in parallel with the authentic samples A, B and C under the identical conditions, the positions of the respective components in the unknown sample can be identified easily and accurately to specify the unknown substance X'.

EXAMPLE 2

(Plate with the linear grooves in the direction parallel to the development direction)

Figure 2:
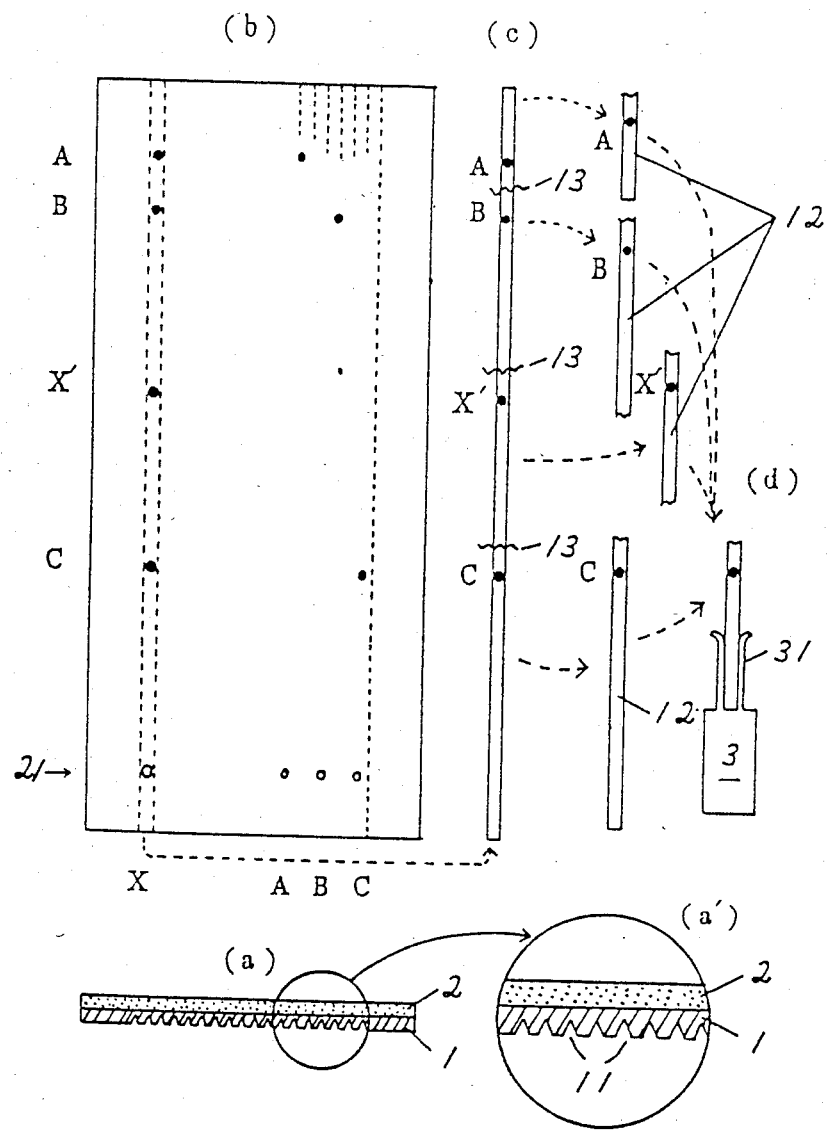

FIG. 2 schematically illustrates this plate. Reference characters and numerals identical with those used in FIG. 1 are also used here. Therefore, most of the above illustration can be applied to that of this example without any alterlation. The difference is that the linear grooves 11 are provided in the direction parallel to the chromatogram development direction instead of that which crosses the latter direction at right angle. By so arranging, the strip (c) resulting from the cleaving operation carries the spots of all substances included in the sample. When this strip is subjected to FID, an FID chart which represents all substances in sequence is obtained. Thereafter, it can be shortened at a position of, for example, the wave line 13 to be subjected to MS as has been described with reference to Example 1.

In addition, although the graphical representation is omitted, additional row of linear grooves other than the abovementioned ones may be engraved with advantages. The former linear grooves cross the latter at right angle and have larger spacings between the adjoining two than those held by the latter. By so arranging, the cloven strips can be cut easily at the abovementioned wave line cutting point 13.

EXAMPLE 3

(Plate with concentrating zone)

A plate as shown in either of FIGS. 1 and 2 is modified to have an adsorbent layer divided into a concentrating zone and a developing zone; the former is occupying an area of about 25 mm in width from one end of the plate along the lengthwise direction and the latter is occupying the rest.

The site of titrating sample is in the abovementioned concentrating zone and near the borderline between that and the developing zone. In the case of using the plate of this example, since the sample is separated to form rectangular and dense spots after being separated, the most advantageous utilization of the cleavage of the plate into strips is made possible. This is the chracteristic point of the present invention.

The detail, methods of preparation and use are as those described with reference to Examples 1 and 2 above, though some deviation from those will be described in detail together with Measurement 2 which follows.

In the following description, the practical advantages of the plates, whose construction has briefly been illustrated in each of the abovementioned Examples, will now be indicated by way of Measurements. Under the headings, the details of the plate used in the actual measurements are described and discussed together with the chromatographic separation of mixture samples on these plates, the FID detection and the results of the mass spectrometry analysis which uses the strips carrying the developed chromatogram.

MEASUREMENT 1

Plate, used (those of Examples 1 and 2)
(1) Support: Soda lime glass (50×200×2 mm)
(2) Linear grooves: spacings 2 mm, depth 1 mm
(3) Adsorbent: Kieselgel H 60, available from Merck A. G.
(4) Fluorescent material: $Zn_2SiO_4/Mn$
(5) Binding agent: Soda lime glass powder (mean diameter: 7–8 μm)
(6) Mixing ratio: adsorbent:bindng agent:fluorescent material=1:3–4:0.25
(7) Thin layer: Prepared by sintering method (as described in Japanese Pat. No. 657,467), baked at 680° C. for 10 min. to obtain a thin layer of a thickness 200 μm (after being sintered).

SAMPLE (1) (MIXTURE CONTAINING BENZODIAZEPINES, 1)

Figure 3:
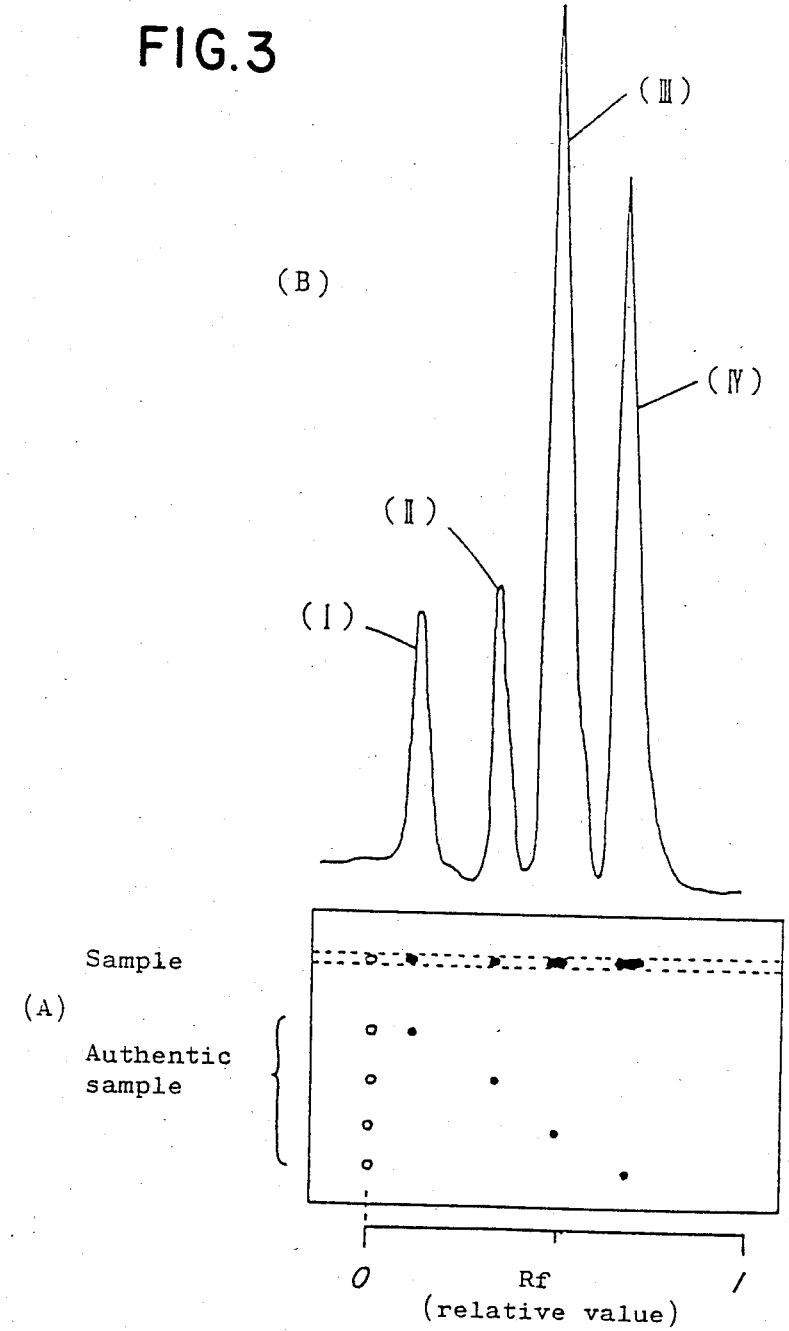
FIG. 3 is a chromatogram (A) and an FID chart (B) of the mixture sample (1) and the authentic samples, FIGS. 4-7, each is a mass spectrum which corresponds to the components (I),(II),(III) or (IV) of the mixture sample (1) or the authentic samples.

In FIG. 3, A chromatogram (A) of the mixture sample (1) and the authentic samples (reference substance) and an FID chart (B) obtained with a cloven strip thereof are comparatively shown.

Chromatography: Developing solvent; dichloromethane:methanol:ethyl acetate:n-hexane=12:1:3:3
FID: Iatoroscan (available from Iatoron K.K.)

As shown by the chromatogram in FIG. 3(A), in the case of using the plate prepared in accordance with the present invention, the unknown sample can be developed simultaneously with the authentic samples under the same conditions and after confirming the existence of a specific substance by comparing the Rf value of the sample, the plate can be cloven into strips which carry the target components of the sample.

In the case of the plate of the type disclosed in Example 1, the plate can be cloven along the direction which crosses the development direction at a right angle to give a sample holder for a mass spectrometer. On the other hand, in the case of an Example 2 type plate, the sample holding strip can be prepared by cleaving the plate along a direction parallel to the development direction to make a stick or rod for FID. The stick is used to give an FID chart as shown in FIG. 3(B). Meanwhile, a strip which had been parallel to the stick before the cleavage can be shortened to a convenient length for the sample holder for mass spectrometer.

Figure 4:
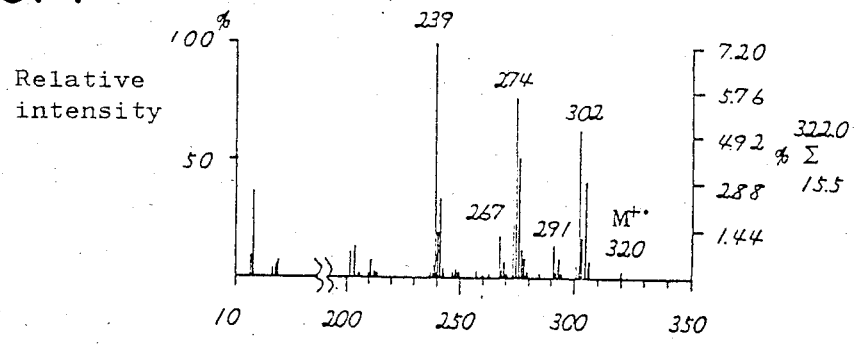
Figure 5:
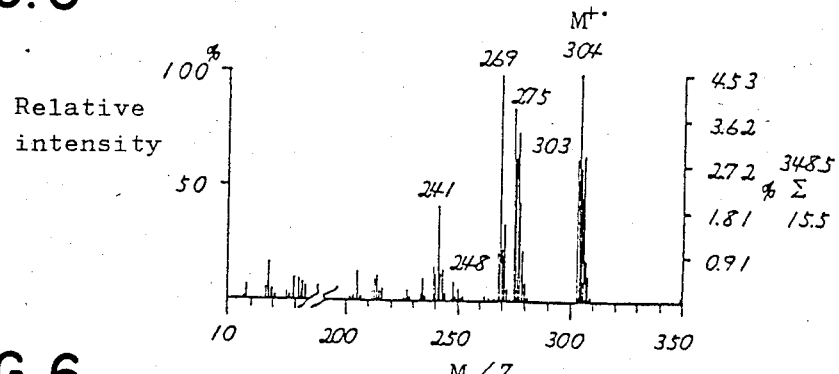
Figure 6:
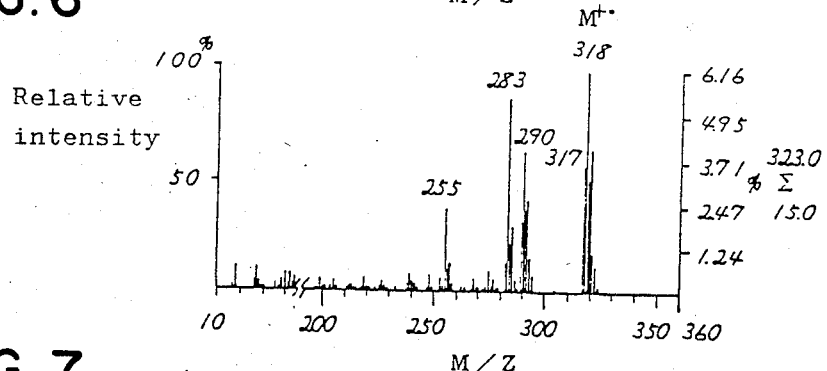
Figure 7:
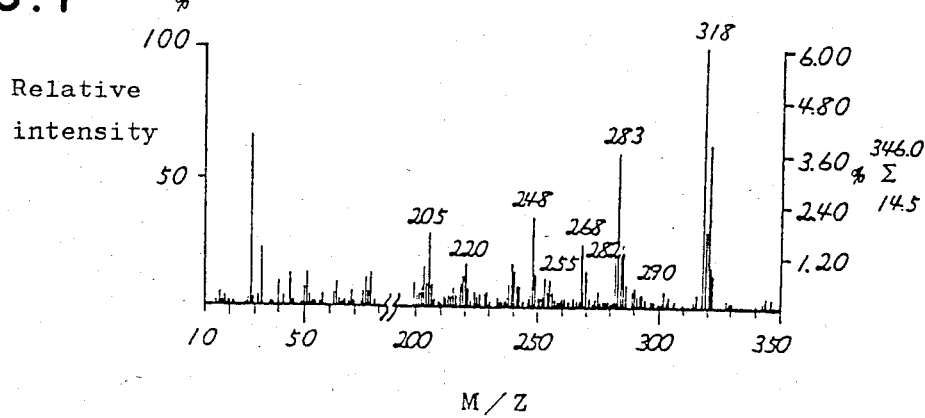

Mass spectra of the respective components of the mixture sample are shown in FIGS. 4–7. FIG. 4 is a mass spectrum of lorazepam which corresponds to the first spot (I) of the chromatogram (FIG. 3(A), an FID chart of which is FIG. 3(B)), FIG. 5 is that of chlorodesmethyldiazepam of spot (II), FIG. 6 is that of chlorodiazepam of spot (III) and FIG. 7 is that of aminoquinolone derivative of spot (IV).

Of these components, in the cases of performing the known GC/MS on the chlorodiazepam (III) and aminoquinolone derivative (IV), the mass spectra similar to those obtained by using the plate of the present invention (FIGS. 6 and 7) are obtained without being subjected to alteration. Namely:

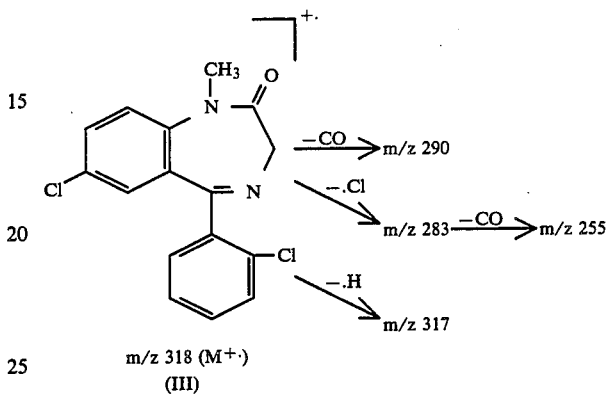

m/z 318 (M+·)
(III)

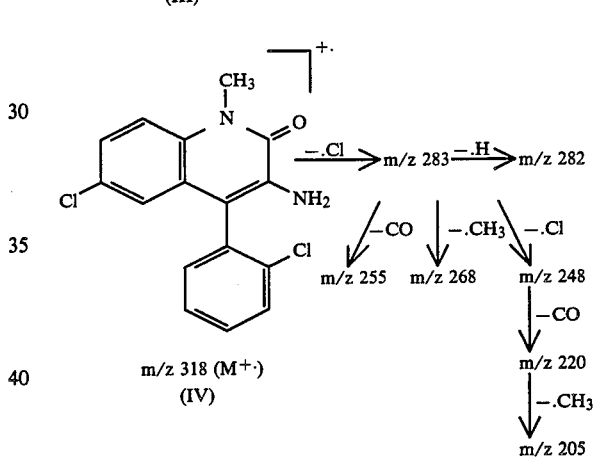

m/z 318 (M+·)
(IV)

Incidentally, fragmentation of the main peaks in the mass spectrum (FIG. 4) of lorazepam in the case wherein lorazepam is separated by using the plate of the present invention is shown by the following formulae. As shown, a molecular ion is obtained as in the case of a conventional direct introduction method.

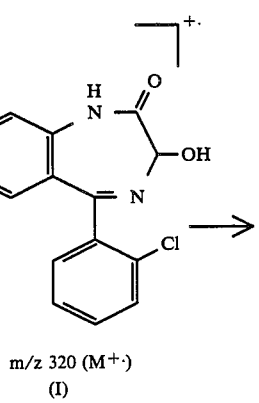

m/z 320 (M+·)
(I)

-continued

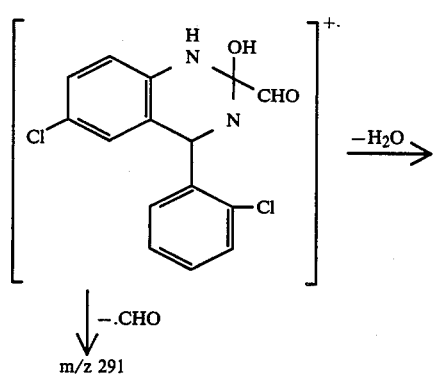

↓ −.CHO m/z 291

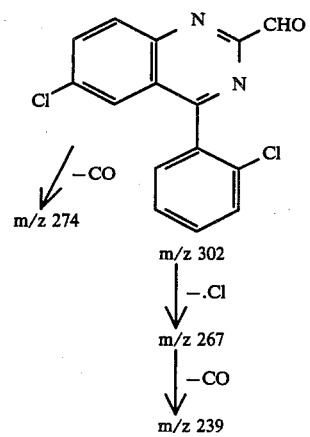

m/z 274 ←−CO− m/z 302
↓ −.Cl
m/z 267
↓ −CO
m/z 239

On the contrary, if it is subjected to GC/MS, dehydration takes place first and the peaks of m/z 320 and m/z 291 disappear (spectrum, omitted).

Fragmentation of the main peaks in the mass spectrum (FIG. 5) of chlorodesmethyldiazem (II) is similar to that of direct introduction and is shown in the following formulae:

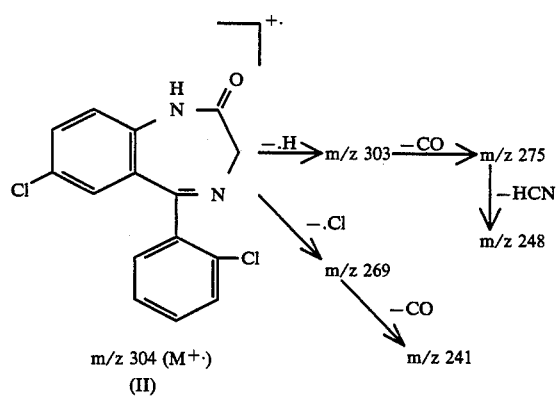

However, in the case of GC/MS, the compound is partly decomposed by heat as shown in the following formula (deduction) to give a different mass spectrum (omitted).

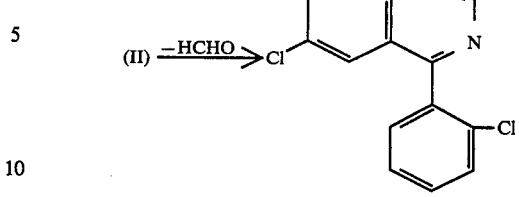

SAMPLE (2) (MIXTURE CONTAINING BENZODIAZEPINES, 2)

Figure 8:
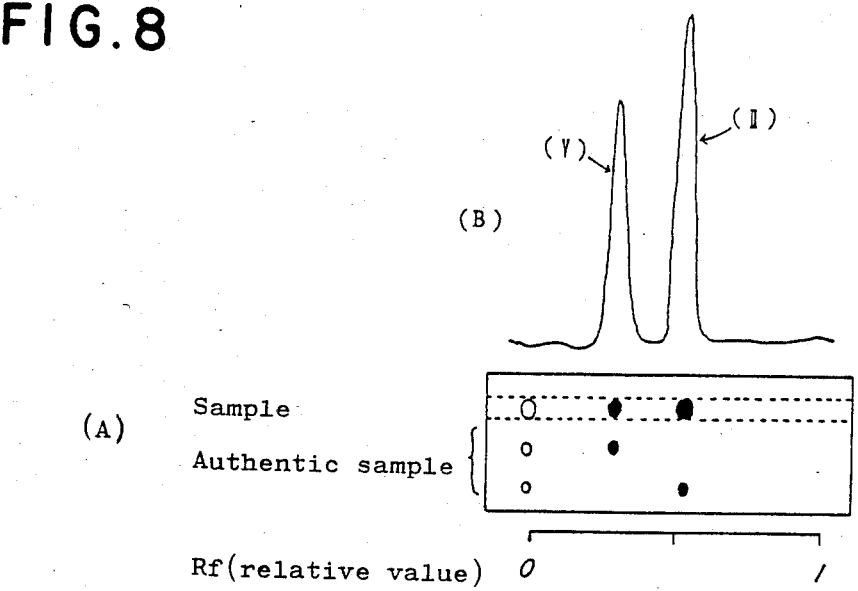
FIG. 8 is a chromatogram (A) and an FID chart (B) of the mixture sample (2) and the authentic samples.

In FIG. 8, chromatogram (A) of the mixture sample (2) and authentic samples developed on the plate of the present invention (Example 2 type) and an FID chart (B) obtained with the strips (FIG. 2(C)) are comparatively shown.

Figure 9:
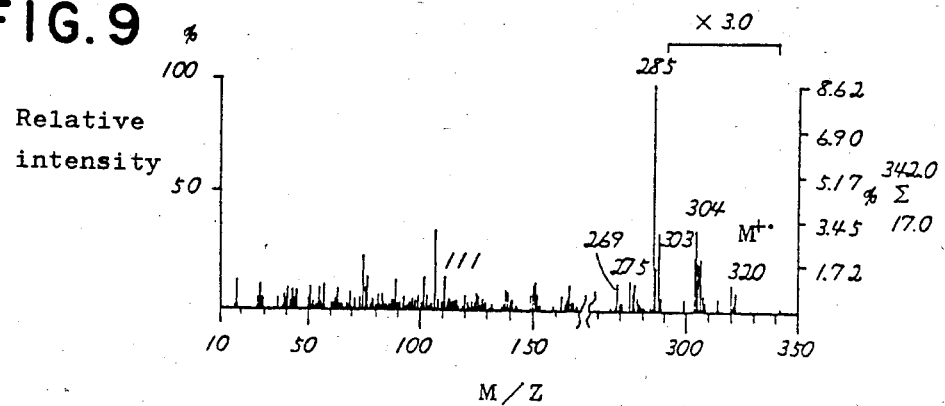
FIG. 9 is a mass spectrum which corresponds to the component (V) in the mixture sample (2) and FIG. 10 is a chromatogram (A) and an FID chart (B) of the mixture sample (3) and the authentic samples.

Chromatography: Developing solvent, dichloromethane:methanol:ethyl acetate:n-hexane=32:1:3:3
FID: Iatroscan Of the abovementioned mixture sample, a mass spectrum of chlorodemoxepam (V) which corresponds to the first spot is shown in FIG. 9. Fragmentation of the main peaks of the compound is as shown in the following formulae which support the detection of molecular ion. (Since chlorodesmethyldiazepam (II) which corresponds to the second spot is identical to that shown in FIG. 5, it is omitted)

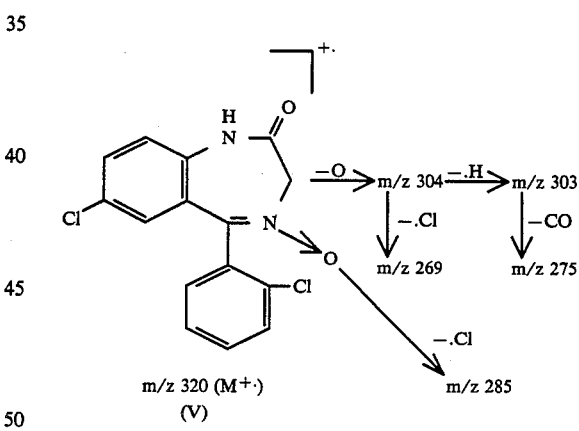

In the case of performing GC/MS on this sample, chlorodemoxepam (V) is decomposed by heat during the GC process to give no molecular ion but to give a spectrum similar to that of (II). (Spectra of more highly decomposed products (unidentified) are also obtained).

SAMPLE (3) (STEROIDAL MIXTURES)

Figure 10:
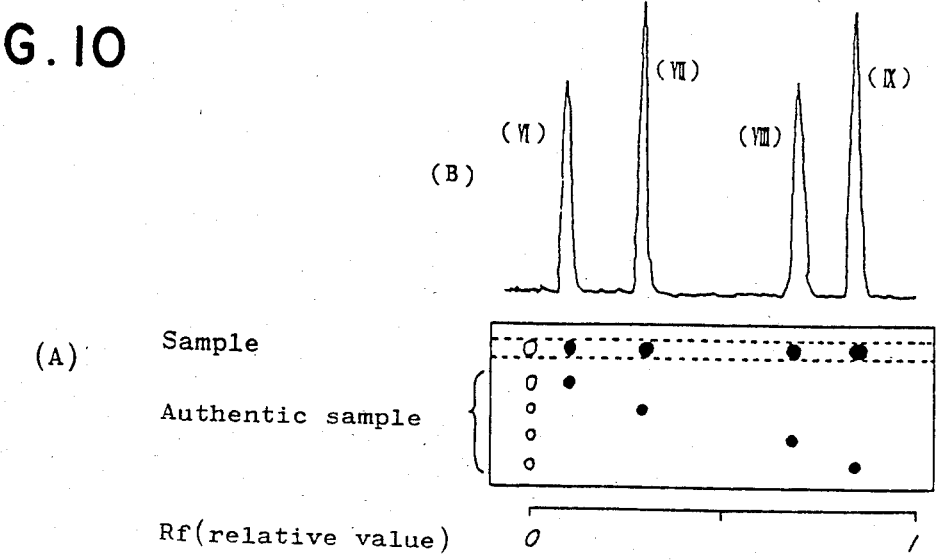

A chromatogram (A) and an FID chart (B) shown in FIG. 10 are obtained by performing a series of experiments similar to the abovementioned Measurement on this sample (Mixture sample (3)). Results of mass spectrometric measurements of the respective spots (mass number (m/z) and relative intensity) are as follows:

First spot (VI) Hydrocortisone:

-continued

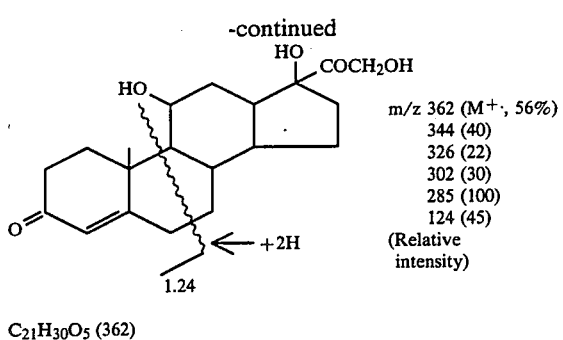

m/z 362 (M+, 56%)
344 (40)
326 (22)
302 (30)
285 (100)
124 (45)
(Relative intensity)

$C_{21}H_{30}O_5$ (362)

Second spot (VII) Cortisone:

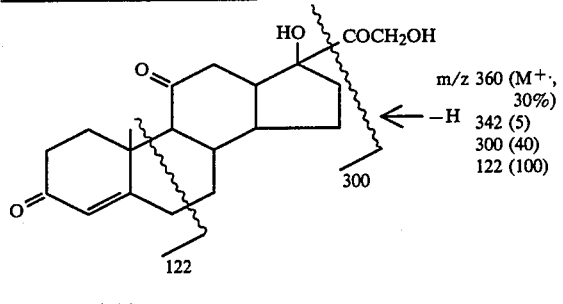

m/z 360 (M+, 30%)
342 (5)
300 (40)
122 (100)

$C_{21}H_{28}O_5$ (360)

Third spot (VIII) Teststerone:

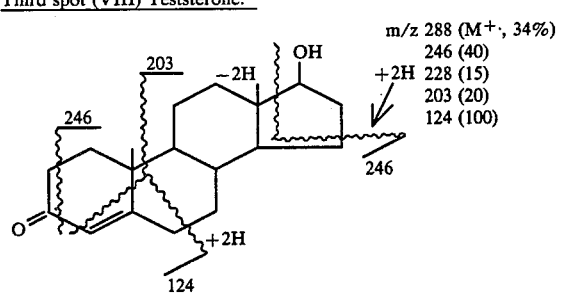

m/z 288 (M+, 34%)
246 (40)
228 (15)
203 (20)
124 (100)

$C_{19}H_{28}O_2$ (288)

Fourth spot (IX) Progesterone:

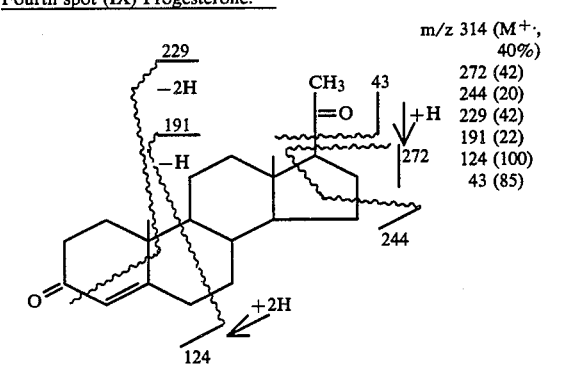

m/z 314 (M+, 40%)
272 (42)
244 (20)
229 (42)
191 (22)
124 (100)
43 (85)

$C_{21}H_{30}O_2$ (314)

Plate, used (One with concentrating zone of Example 3)
(1) Support plate: identical to that used in Measurement 1
(2) Linear grooves: ditto.
(3) Concentrating zone (25 mm in width from one end): Mixture of quartz powder (15–20 μm):UV transmitting glass powder (7–8 μm):Fluorescent material (the same as that used in Measurement 1)=4:1:0.25.

(4) Developing zone: Mixture of Kieselgel H60, of Merck A. G.:UV transmitting glass powder (7–8 μm):Fluorescent material (as disclosed above)=1:3–4:0.25
(5) Formation of the thin layer: (Sintering method as that of Measurement 1, but baked at 720° C. for 12 min.)

By separating the steroidal mixture sample used in Measurement 1, which uses the plate prepared in the abovementioned manner, the following chromatographic results are obtained.
Developing solvent: Chloroform:methanol=100:1
Rf value: Hydrocortisone, 0.025; Cortisone, 0.07; Teststerone, 0.44; Progesterone, 0.72.

Although the Rf value of hydrocortisone is close to that of cortisone, the former is sharply separated from the latter on the cut strip by virtue of the concentrating function of the plate. The results of mass spectrometry are the same as previously described.

What is claimed is:
1. A chromatographic plate for use as a sample holder in mass spectrometry analysis, comprising
  a support layer of sheet glass;
  a sintered chromatographically-active adsorbent layer on the front of the support, said adsorbent layer containing a chromatographically-active adsorbent material, a glass powder binding agent and a fluorescent material powder;
  a plurality of linear grooves engraved on the rear of the plate for guiding a cutter whereby a strip containing samples of the material to be analyzed is cloven.
2. The plate as claimed in claim 1, wherein each of said grooves has a uniform depth of a half or less the thickness of the support.
3. The plate as claimed in claim 1, wherein said grooves comprise first and second rows of the linear grooves crossing each other at right angles.
4. The plate as claimed in claim 3, wherein said grooves in the first row have larger spacings between the adjoining two than those held by the grooves in the second row.
5. The plate as claimed in claim 1, wherein the adsorbent layer carried by the front of the support is divided into a chromatogram development zone and a preparatory concentrating zone sharing a common boundary with said chromatogram development zone.
6. The plate as claimed in claim 5, wherein the adsorbent in said preparatory concentrating zone is less chromatographically-active than that in said chromatogram development zone.
7. The plate as claimed in claim 6, wherein said concentrating zone is composed solely of a sintered body of glass powder covering the support.
8. The chromatographic plate as claimed in claim 1, wherein the chromatographically-active adsorbent material is a member selected from the group consisting of silica gel, alumina, diatomaceous earth, zeolite, aluminum silicate and porous glass powder.
9. The chromatographic plate as claimed in claim 1, wherein the glass powder binding agent is soda lime glass powder.
10. A method for conducting chromatographical analysis of a sample or plurality of samples comprising:
  placing a sample or plurality of samples onto the bottom of a chromatographic plate, said plate having a support layer of sheet glass, a sintered chromatographically-active adsorbent layer on the front of the support, said adsorbent layer containing a chromatographically-active adsorbent material, a glass powder binding agent and a fluorescent material powder; and a plurality of linear grooves engraved on the rear of the plate;

subjecting said sample or said plurality of samples to ascending chromatographic development in a solvent system, thereby separating said sample or said plurality of samples into component substances; and isolating said component substances by cloving said plate along said grooves.

11. The method as claimed in claim 10, wherein said component substances are subsequently subjected to mass spectrometry analysis.

12. The method as recited in claim 10, wherein the plurality of linear grooves engraved on the rear of the plate comprise first and second rows of the linear grooves crossing each other at right angles.

* * * * *